United States Patent
Metzger

(10) Patent No.: US 7,837,690 B2
(45) Date of Patent: Nov. 23, 2010

(54) METHOD AND APPARATUS FOR LESS INVASIVE KNEE RESECTION

(75) Inventor: Robert Metzger, Walkarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 10/345,102

(22) Filed: Jan. 15, 2003

(65) Prior Publication Data
US 2004/0138670 A1    Jul. 15, 2004

(51) Int. Cl.
*A61B 17/15* (2006.01)
(52) U.S. Cl. .................................................. 606/87
(58) Field of Classification Search ............... 606/86, 606/87, 88, 89, 79, 82, 86 R; 83/583, 613
See application file for complete search history.

(56) References Cited

U.S. PATENT DOCUMENTS

| | | | |
|---|---|---|---|
| 1,763,730 A | 6/1930 | Von Lackum |
| 1,959,615 A | 5/1934 | Derrah |
| 2,433,815 A | 12/1947 | Laforge |
| 2,455,655 A | 12/1948 | Carroll |
| 2,702,550 A | 2/1955 | Rowe |
| 2,724,326 A | 11/1955 | Long |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie |
| 3,624,747 A | 11/1971 | McKnight |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee |
| 3,869,731 A | 3/1975 | Waugh et al. |
| 3,903,549 A | 9/1975 | Deyerle |

(Continued)

FOREIGN PATENT DOCUMENTS

CH    117960    5/1927

(Continued)

OTHER PUBLICATIONS

Biomet, Inc., Genus™ brochure entitled "Uni Knee System", Nov. 15, 1998.

(Continued)

*Primary Examiner*—Eduardo C Robert
*Assistant Examiner*—David Comstock
(74) *Attorney, Agent, or Firm*—Harness, Dickey

(57) ABSTRACT

Various tools and portions are used to perform a resection of a portion of the anatomy for preparation of the implants of a prosthetic. Various saw blades having selected geometries and shapes can be used to assist in the resection of an anatomy to provide for implantation of a prosthetic. In addition, a cutting block assembly is provided wherein a cutting block is translatably mounted on a rail. The rail is fixed relative a portion of the anatomy. Therefore, once the rail is fixed, the cutting block can move to a selected position and held there without moving the rail.

40 Claims, 7 Drawing Sheets

U.S. PATENT DOCUMENTS

| | | |
|---|---|---|
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom |
| 3,994,287 A | 11/1976 | Turp |
| 4,053,953 A | 10/1977 | Flom |
| 4,055,862 A | 11/1977 | Farling |
| 4,081,866 A | 4/1978 | Upshaw et al. |
| 4,085,466 A | 4/1978 | Goodfellow |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle |
| 4,311,145 A | 1/1982 | Esty |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano |
| 4,501,269 A | 2/1985 | Bagby |
| 4,509,518 A | 4/1985 | McGarry |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz |
| 4,565,192 A | 1/1986 | Shapiro |
| 4,567,886 A | 2/1986 | Petersen |
| 4,574,794 A | 3/1986 | Cooke et al. |
| 4,608,052 A | 8/1986 | Van Kampen et al. |
| 4,619,391 A | 10/1986 | Sharkany |
| 4,624,254 A | 11/1986 | McGarry |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany |
| 4,678,470 A | 7/1987 | Nashef et al. |
| 4,682,598 A | 7/1987 | Beraha |
| 4,685,460 A | 8/1987 | Thornton |
| 4,703,751 A | 11/1987 | Pohl |
| 4,711,233 A | 12/1987 | Brown |
| 4,718,413 A | 1/1988 | Johnson |
| 4,718,916 A | 1/1988 | Morscher |
| 4,739,751 A | 4/1988 | Sapega et al. |
| 4,794,854 A | 1/1989 | Swaim |
| 4,817,602 A | 4/1989 | Beraha |
| 4,834,757 A | 5/1989 | Brantigan |
| 4,838,891 A | 6/1989 | Bränemark et al. |
| 4,863,472 A | 9/1989 | Tormala et al. |
| 4,888,022 A | 12/1989 | Huebsch |
| 4,911,721 A | 3/1990 | Bränemark et al. |
| 4,935,023 A | 6/1990 | Whiteside et al. |
| 4,936,852 A | 6/1990 | Kent |
| 4,950,296 A | 8/1990 | McIntyre |
| 4,952,213 A | 8/1990 | Bowman et al. |
| 4,961,740 A | 10/1990 | Ray et al. |
| 4,961,954 A | 10/1990 | Goldberg |
| 4,964,865 A | 10/1990 | Burkhead |
| 4,979,949 A | 12/1990 | Matsen, III et al. |
| 4,979,957 A | 12/1990 | Hodorek |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen |
| 5,035,700 A | 7/1991 | Kenna |
| 5,060,678 A | 10/1991 | Bauman |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,092,869 A | 3/1992 | Waldron |
| 5,098,436 A | 3/1992 | Ferrante et al. |
| 5,098,437 A | 3/1992 | Kashuba |
| 5,099,859 A | 3/1992 | Bell |
| 5,100,689 A | 3/1992 | Goldberg |
| 5,101,720 A | 4/1992 | Bianchi |
| 5,108,441 A | 4/1992 | McDowell |
| 5,111,987 A | 5/1992 | Moeinzadeh |
| 5,122,144 A | 6/1992 | Bert et al. |
| 5,123,906 A | 6/1992 | Kelman |
| 5,129,909 A | 7/1992 | Sutherland |
| 5,152,744 A | 10/1992 | Krause |
| 5,152,778 A | 10/1992 | Bales |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith |
| 5,171,243 A | 12/1992 | Kashuba |
| 5,171,244 A | 12/1992 | Caspari et al. |
| 5,171,276 A | 12/1992 | Caspari et al. |
| 5,174,300 A | 12/1992 | Bales |
| 5,176,702 A | 1/1993 | Bales |
| 5,178,622 A | 1/1993 | Lehner |
| 5,183,053 A | 2/1993 | Yeh |
| 5,183,464 A | 2/1993 | Dubrul |
| 5,186,178 A | 2/1993 | Yeh |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch |
| 5,204,106 A | 4/1993 | Schepers et al. |
| 5,207,680 A * | 5/1993 | Dietz et al. .................. 606/86 |
| 5,207,692 A | 5/1993 | Kraus |
| 5,217,463 A | 6/1993 | Mikhail |
| 5,228,459 A | 7/1993 | Caspari et al. |
| 5,234,433 A | 8/1993 | Bert et al. |
| 5,242,448 A | 9/1993 | Pettine et al. |
| 5,258,004 A | 11/1993 | Bales |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox |
| D343,247 S | 1/1994 | Walen |
| 5,275,166 A | 1/1994 | Vaitekunas |
| 5,275,603 A | 1/1994 | Ferrante et al. |
| 5,282,803 A | 2/1994 | Lackey |
| 5,285,773 A | 2/1994 | Bonutti |
| 5,293,878 A | 3/1994 | Bales |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,322,505 A | 6/1994 | Krause |
| 5,329,846 A | 7/1994 | Bonutti |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,402 A | 11/1994 | Mumme et al. |
| 5,368,599 A | 11/1994 | Hirsch |
| 5,379,133 A | 1/1995 | Kirk |

| Patent No. | Kind | Date | Inventor | | Patent No. | Kind | Date | Inventor |
|---|---|---|---|---|---|---|---|---|
| 5,382,249 | A * | 1/1995 | Fletcher ............ 606/79 | | 5,866,415 | A | 2/1999 | Villeneuve |
| 5,383,937 | A | 1/1995 | Mikhail | | 5,871,493 | A | 2/1999 | Sjostrom |
| 5,390,683 | A | 2/1995 | Pisharodi | | 5,879,354 | A | 3/1999 | Haines et al. |
| 5,395,376 | A | 3/1995 | Caspari et al. | | 5,888,219 | A | 3/1999 | Bonutti |
| D358,647 | S | 5/1995 | Cohen | | 5,899,914 | A | 5/1999 | Zirps |
| 5,423,827 | A | 6/1995 | Mumme et al. | | 5,908,424 | A | 6/1999 | Bertin et al. |
| 5,425,355 | A | 6/1995 | Kulick | | 5,911,723 | A | 6/1999 | Ashby et al. |
| 5,425,745 | A | 6/1995 | Green | | 5,913,874 | A | 6/1999 | Berns |
| 5,445,639 | A | 8/1995 | Kuslich | | 5,916,219 | A | 6/1999 | Matsuno et al. |
| 5,454,365 | A | 10/1995 | Bonutti | | 5,921,990 | A | 7/1999 | Webb |
| 5,454,815 | A | 10/1995 | Geisser | | 5,925,049 | A | 7/1999 | Gustilo et al. |
| 5,454,816 | A | 10/1995 | Ashby | | 5,961,499 | A | 10/1999 | Bonutti |
| 5,456,268 | A | 10/1995 | Bonutti | | 5,997,566 | A | 12/1999 | Tobin |
| 5,456,720 | A | 10/1995 | Schultz | | 6,007,537 | A | 12/1999 | Burkinshaw et al. |
| 5,472,415 | A | 12/1995 | King | | 6,012,456 | A | 1/2000 | Schuerch |
| 5,484,095 | A | 1/1996 | Green | | 6,015,419 | A | 1/2000 | Strome |
| 5,490,854 | A | 2/1996 | Fisher et al. | | 6,019,767 | A | 2/2000 | Howell |
| 5,497,933 | A | 3/1996 | DeFonzo | | 6,022,350 | A | 2/2000 | Ganem |
| 5,507,763 | A | 4/1996 | Petersen et al. | | 6,056,754 | A | 5/2000 | Haines et al. |
| 5,514,139 | A | 5/1996 | Goldstein et al. | | 6,059,817 | A | 5/2000 | Bonutti |
| 5,514,143 | A | 5/1996 | Bonutti et al. | | 6,059,831 | A | 5/2000 | Braslow et al. |
| 5,520,692 | A | 5/1996 | Ferrante | | 6,063,095 | A | 5/2000 | Wang et al. |
| 5,520,694 | A | 5/1996 | Dance et al. | | 6,077,270 | A | 6/2000 | Katz |
| 5,522,897 | A | 6/1996 | King | | 6,077,287 | A | 6/2000 | Taylor |
| 5,540,695 | A | 7/1996 | Levy | | 6,086,593 | A | 7/2000 | Bonutti |
| 5,545,222 | A | 8/1996 | Bonutti | | 6,090,122 | A | 7/2000 | Sjostrom |
| 5,549,683 | A | 8/1996 | Bonutti | | 6,099,531 | A | 8/2000 | Bonutti |
| 5,554,169 | A | 9/1996 | Green | | 6,099,532 | A | 8/2000 | Florea |
| 5,569,163 | A | 10/1996 | Francis | | 6,102,850 | A | 8/2000 | Wang et al. |
| 5,570,700 | A | 11/1996 | Vogeler | | 6,106,529 | A | 8/2000 | Techiera |
| 5,578,039 | A | 11/1996 | Vendrely et al. | | 6,118,845 | A | 9/2000 | Simon et al. |
| 5,593,448 | A | 1/1997 | Dong | | 6,120,509 | A | 9/2000 | Wheeler |
| 5,597,379 | A | 1/1997 | Haines et al. | | 6,132,472 | A | 10/2000 | Bonutti |
| 5,609,603 | A | 3/1997 | Linden | | 6,156,070 | A | 12/2000 | Incavo et al. |
| 5,611,802 | A | 3/1997 | Samuelson et al. | | 6,159,246 | A | 12/2000 | Mendes et al. |
| 5,624,463 | A | 4/1997 | Stone | | 6,171,340 | B1 | 1/2001 | McDowell |
| 5,632,745 | A | 5/1997 | Schwartz | | 6,174,321 | B1 | 1/2001 | Webb |
| 5,643,272 | A | 7/1997 | Haines et al. | | 6,185,315 | B1 | 2/2001 | Schmucker et al. |
| 5,649,946 | A | 7/1997 | Bramlet | | 6,187,023 | B1 | 2/2001 | Bonutti |
| 5,653,714 | A * | 8/1997 | Dietz et al. ............ 606/87 | | 6,195,168 | B1 | 2/2001 | De Lega |
| 5,662,710 | A | 9/1997 | Bonutti | | 6,197,064 | B1 | 3/2001 | Haines et al. |
| 5,667,069 | A | 9/1997 | Williams | | 6,198,794 | B1 | 3/2001 | Peshkin et al. |
| 5,667,511 | A | 9/1997 | Vendrely et al. | | 6,211,976 | B1 | 4/2001 | Popovich et al. |
| 5,667,512 | A | 9/1997 | Johnson | | 6,214,051 | B1 | 4/2001 | Badorf |
| 5,667,520 | A | 9/1997 | Bonutti | | 6,228,121 | B1 | 5/2001 | Khalili |
| D385,163 | S | 10/1997 | Hutchins et al. | | 6,258,127 | B1 | 7/2001 | Schmotzer |
| 5,681,316 | A | 10/1997 | DeOrio et al. | | 6,277,136 | B1 | 8/2001 | Bonutti |
| 5,683,398 | A | 11/1997 | Carls et al. | | 6,290,703 | B1 | 9/2001 | Ganem |
| 5,694,693 | A | 12/1997 | Hutchins et al. | | 6,290,704 | B1 | 9/2001 | Burkinshaw et al. |
| 5,702,447 | A | 12/1997 | Walch | | 6,325,806 | B1 | 12/2001 | Fox |
| 5,702,475 | A | 12/1997 | Zahedi | | 6,328,572 | B1 | 12/2001 | Higashida |
| 5,704,941 | A | 1/1998 | Jacober et al. | | 6,338,737 | B1 | 1/2002 | Toledano |
| 5,707,350 | A | 1/1998 | Krause | | 6,358,266 | B1 | 3/2002 | Bonutti |
| 5,712,543 | A | 1/1998 | Sjostrom | | 6,361,565 | B1 | 3/2002 | Bonutti |
| 5,716,360 | A | 2/1998 | Baldwin et al. | | 6,391,040 | B1 | 5/2002 | Christoudias |
| 5,718,708 | A | 2/1998 | Webb | | 6,406,495 | B1 | 6/2002 | Schoch |
| 5,723,331 | A | 3/1998 | Tubo | | 6,409,722 | B1 | 6/2002 | Hoey |
| 5,733,292 | A | 3/1998 | Gustilo et al. | | 6,423,063 | B1 | 7/2002 | Bonutti |
| 5,749,876 | A | 5/1998 | Duvillier et al. | | 6,431,743 | B1 | 8/2002 | Mizutani |
| 5,755,731 | A | 5/1998 | Grinberg | | D462,767 | S | 9/2002 | Meyer |
| 5,755,791 | A | 5/1998 | Whitson | | 6,458,135 | B1 | 10/2002 | Harwin et al. |
| 5,755,803 | A | 5/1998 | Haines et al. | | 6,468,280 | B1 | 10/2002 | Saenger et al. |
| 5,769,855 | A | 6/1998 | Bertin et al. | | 6,468,289 | B1 | 10/2002 | Bonutti |
| 5,769,899 | A | 6/1998 | Schwartz | | 6,478,799 | B1 | 11/2002 | Williamson |
| 5,772,594 | A | 6/1998 | Barrick | | 6,482,209 | B1 | 11/2002 | Engh et al. |
| 5,788,700 | A | 8/1998 | Morawa et al. | | 6,500,181 | B1 | 12/2002 | Portney |
| 5,810,827 | A | 9/1998 | Haines et al. | | 6,503,267 | B2 | 1/2003 | Bonutti et al. |
| 5,817,097 | A | 10/1998 | Howard et al. | | 6,554,837 | B1 | 4/2003 | Hauri et al. |
| 5,817,109 | A | 10/1998 | McGarry | | 6,554,838 | B2 | 4/2003 | McGovern et al. |
| 5,842,477 | A | 12/1998 | Naughton et al. | | 6,558,391 | B2 | 5/2003 | Axelson et al. |
| 5,846,931 | A | 12/1998 | Hattersley | | 6,575,982 | B1 | 6/2003 | Bonutti |
| 5,860,980 | A | 1/1999 | Axelson, Jr. et al. | | 6,602,259 | B1 | 8/2003 | Masini |
| 5,860,981 | A | 1/1999 | Bertin et al. | | 6,620,181 | B1 | 9/2003 | Bonutti |

| | | | |
|---|---|---|---|
| 6,632,225 | B2 | 10/2003 | Sanford et al. |
| 6,635,073 | B2 | 10/2003 | Bonutti |
| 6,673,077 | B1 | 1/2004 | Katz |
| 6,676,662 | B1 * | 1/2004 | Bagga et al. .................. 606/87 |
| 6,695,848 | B2 | 2/2004 | Haines |
| 6,702,821 | B2 | 3/2004 | Bonutti |
| 6,770,078 | B2 | 8/2004 | Bonutti |
| 6,979,299 | B2 | 12/2005 | Peabody et al. |
| 7,029,477 | B2 | 4/2006 | Grimm |
| 7,172,599 | B2 | 2/2007 | Steffensmeier et al. |
| 7,261,719 | B1 | 8/2007 | Twomey et al. |
| 7,344,541 | B2 | 3/2008 | Haines et al. |
| 7,488,324 | B1 | 2/2009 | Metzger et al. |
| 2001/0018589 | A1 | 8/2001 | Muller |
| 2001/0034554 | A1 | 10/2001 | Pappas |
| 2001/0037155 | A1 | 11/2001 | Merchant |
| 2002/0029038 | A1 | 3/2002 | Haines |
| 2002/0029045 | A1 | 3/2002 | Bonutti |
| 2002/0052606 | A1 | 5/2002 | Bonutti |
| 2002/0116023 | A1 | 8/2002 | Fletcher et al. |
| 2002/0173797 | A1 | 11/2002 | Van Zile |
| 2002/0198529 | A1 | 12/2002 | Masini |
| 2002/0198531 | A1 | 12/2002 | Millard et al. |
| 2003/0028196 | A1 | 2/2003 | Bonutti |
| 2003/0060831 | A1 | 3/2003 | Bonutti |
| 2003/0100906 | A1 | 5/2003 | Rosa et al. |
| 2003/0100907 | A1 | 5/2003 | Rosa et al. |
| 2003/0130665 | A1 | 7/2003 | Pinczewski et al. |
| 2003/0171757 | A1 | 9/2003 | Coon et al. |
| 2003/0212403 | A1 | 11/2003 | Swanson |
| 2003/0216741 | A1 | 11/2003 | Sanford et al. |
| 2003/0220641 | A1 | 11/2003 | Thelen et al. |
| 2003/0225413 | A1 | 12/2003 | Sanford et al. |
| 2004/0039395 | A1 | 2/2004 | Coon et al. |
| 2004/0102785 | A1 | 5/2004 | Hodorek et al. |
| 2004/0220583 | A1 | 11/2004 | Pieczynski et al. |
| 2005/0049603 | A1 | 3/2005 | Calton et al. |
| 2005/0113840 | A1 | 5/2005 | Metzger et al. |
| 2005/0149038 | A1 | 7/2005 | Haines et al. |
| 2005/0149040 | A1 | 7/2005 | Haines et al. |
| 2005/0149042 | A1 | 7/2005 | Metzger |
| 2005/0177170 | A1 | 8/2005 | Fisher et al. |
| 2006/0095049 | A1 | 5/2006 | Zannis et al. |
| 2006/0142774 | A1 | 6/2006 | Metzger |
| 2006/0142778 | A1 | 6/2006 | Dees |
| 2007/0083209 | A1 | 4/2007 | Schenberger et al. |
| 2007/0233140 | A1 | 10/2007 | Metzger et al. |
| 2007/0282451 | A1 | 12/2007 | Metzger et al. |

FOREIGN PATENT DOCUMENTS

| | | |
|---|---|---|
| DE | 337437 | 5/1921 |
| FR | 1111677 | 3/1956 |
| JP | 64-29266 | 1/1989 |
| JP | 2501806 | 6/1990 |
| JP | 3504337 | 9/1991 |
| JP | 7178114 A | 7/1995 |
| WO | WO-8804912 | 7/1988 |
| WO | WO-8909028 | 10/1989 |
| WO | WO-8909028 A1 | 10/1989 |
| WO | WO 96/07361 | 3/1996 |
| WO | WO 97/29703 | 8/1997 |

OTHER PUBLICATIONS

Keys, Graham W., "Reduced Invasive Approach for Oxford II Medial Unicompartmental Knee Replacement—a Preliminary Study," The Knee, (1999) pp. 193-196.

Biomet, Inc., "AGC Distal Fem Cutter for Dr. Hardy", Jun. 22, 1989.

Biomet Orthopedics, Inc., The Oxford™, brochure entitled "Unicompartmental Knee System", Jul. 15, 2004.

Scorpio! Single Axis Total Knee System—Passport Total Knee Instruments—Passport A.R. Surgical Technique by Stryker Howmedica Osteonics, Copyright 2000.

Install/Burstein II Modular Knee System by Zimmer, Inc., Copyright 1989.

Biomet Orthopedics, Inc., Microplasty, brochure entitled "Minimally Invasive Knee Instruments," Feb. 29, 2004.

NexGen System Complete Knee Solution—Design Rationale—Publication date unknown.

NexGen Complete Knee Solution-Extramedullary/Intramedullary Tibial Resector Surgical Technique-Publication date unknown, but before Aug. 1, 2001.

NexGen Complete Knee Solution-Intramedullary Instrumentation Surgical Technique-For the NexGen Cruciate Retaining & Legacy Posterior Stabilized Knee-Publication date unknown, but before Aug. 1, 2001.

NexGen Complete Knee Solution-Multi-Reference 4-in-1 Femoral Instrumentation-Anterior Reference Surgical Technique-Publication date unknown, but before Aug. 1, 2001.

NexGen Complete Knee Solution-Surgical Technique for the LPS-Flex Fixed Bearing Knee-Publication date unknown, but before Aug. 1, 2001.

Operative Arthroscopy-John B. McGinty, M.D.-Department of Orthopaedic Surgery, Medical University of South Carolina, Charleston, South Carolina-copyright 1991 by Raven Press, Ltd. p. 9.

Surgical Navigation for Total Knee Arthroplasty-Believed to have been presented at the American Academy of Orthopedic Surgeons in Feb. 2001.

"Hand Instruments", High Performance, Precision Series brochure by Arthrotek, copyright 2000.

"The Freeman Samuelson Total Knee System," brochure, Biomet, Inc. (1994) 4 pages.

Biomet Orthopedics, Inc., "Microplasty Minimally Invasive Knee Instruments", 2004, pp. 1-12.

"AGC 3000 Intramedullary Surgical Technical Technique Using PMMA Fixation", 1987, Biomet, Inc.

"AGC-S Total Knee System, Surgical Technique for the AGC-S Total Knee System", 1992, Biomet, Inc.

"Anatomic Axial Alignment Instrumentation", 1994, Biomet, Inc.

"The AGC Revision Knee System Surgical Technique", 1997, Biomet, Inc.

"AGC Total Knee System, Intramedulary Without Distractor Surgical Technique", 1989, Biomet, Inc.

"AGC Traditional Surgical Overview", copyright 2001 Biomet Orthopedics, Inc.

AGC Total Knee System, Unicondylar Surgical Overview, Biomet, Inc. (4 pages).

Orthopaedic Update, No. 18, The Fudger™—The Ultimate Weapon in the Femoral Referencing War, Biomet, Inc. (2 pages).

NexGen Complete Knee Solution-Multi-Reference 4-in-1 femoral Instrumentation-Anterior Reference Surgical Technique-Publication date unknown, but before Aug. 1, 2001.

Scorpio! Single Axis Total Knee System—Passport Total Knee Instruments—Passport A.R. Surgical Technique by Stryker Howmedica Osteonics, Copyright 2000.

Install/Burstein II Modular Knee System by Zimmer, Inc. copyright 1989.

MIS Minimally Invasive Solution The M/G Unicompartmental Knee Minimally Invasive Surgical Technique, by Zimmer copyright 2000.

Simple Instruments Surgical Technique for the Knee, copyright 2000 Biomet, Inc.

MIS Minimally Invasive Solution—The M/G Unicompartmental Knee by Zimmer, 4 sheets.

* cited by examiner

METHOD AND APPARATUS FOR LESS INVASIVE KNEE RESECTION

FIELD

The present claims relate to orthopedic surgery, and particularly to, knee resection procedures and instruments.

BACKGROUND

The human anatomy includes many articulating portions. For example, the femur and the tibia form a knee joint in the human anatomy. The femur and tibia articulate relative to one another during many activities, such as walking or kneeling. Nevertheless, over time, disease and/or injury can deteriorate the knee joint, such that articulation of the joint becomes painful or impractical. When such injuries occur, anatomical replacements, particularly prosthetics, can be placed in the femur, tibia, or both. The prosthetics may replace the articulating portions and allow a substantially natural articulation of the joint. Replacing the damaged portions allow for a much easier and more practical articulation of the knee joint to assist the individual in returning to a more natural lifestyle.

To replace joints, such as the knee joint, the original or natural anatomy, including boney portions, must first be removed or resected. For example, the knee joint includes the condyles of the femur and the tibial plateau. The condyles of the femur articulate with a meniscus in the knee joint, which is supported by the tibia. To replace the knee joint, particularly replacing the articulating portions, the tibial plateau and the condyles of the femur are generally removed.

Often, the condyles of the femur are removed with a saw blade or other reaming devices. The femur is shaped to receive the prosthetic, which will simulate the condyles of the femur after implantation. Specifically, the femur must be shaped to substantially compliment the superior portion of the femoral implant to ensure a substantially tight and secure fit between the femoral implant and the femur.

Likewise, the tibia must be resected to properly receive the tibial implant. This often requires removing the superior portion of the tibia so that an implant can be securely fixed to the superior portion of the resected tibia. A saw blade or other reaming device is used to remove the superior portion and substantially flatten the superior portion of the tibia. After this, a tibial implant can be implanted onto the tibia and securely fixed in place.

To perform such knee replacements, and other joint replacements, it is desirable to allow a less invasive procedure. During less invasive surgeries, the incision to insert the tools is kept to a minimum. Likewise, the tools and instruments used to perform the procedure are optimized to provide minimal abrasion and trauma to the surrounding soft tissue. Therefore, it is desirable to provide instruments that can be used through very small incisions to decrease the amount of trauma to the soft tissue. Similarly, the ease of use of the smaller instruments is desired to be enhanced to allow for an efficient and proper use during the surgical procedure.

SUMMARY

Devices and methods to be used during a minimally invasive surgery for a joint resection include a saw blade and cutting block. The saw blade for use in a minimally invasive surgery includes a narrowed neck or body to allow for an ease of use through a small incision. The head, which include cutting teeth, can be broader than the neck of the saw blade. The narrowed neck allows the blade to translate in a small incision, without abrading the soft tissue. A second saw blade may include an angled neck. The angled neck may also be narrowed relative to the cutting head, but the angled neck allows the cutting head to be laterally offset from the power tool. Therefore, all portions of a joint, such as the knee joint, can be reached from a single incision, which is placed medially or laterally on the knee. In conjunction with the above-described saw blades and other generally known saw blades, a cutting block, which is able to translate medially and laterally is also described. Specifically, a cutting block can be mounted to the inferior portion of the femur and used as a cutting guide during the resection procedure. The cutting block may be moved medially/laterally, along with the incision and soft tissue, such that the cutting guide or cutting block need not be repositioned other than being slid along a rail.

A first embodiment includes a guide block assembly for assisting in resecting a boney structure. The assembly comprises a track member having a fixation section to fix the track member to the boney structure and a track translation section. The assembly also includes a cutting block having a guiding section adapted to guide a cutting member and a guide translation section to operably engage the track translation section. The track translation section and the guide translation section operably interact to allow the cutting block to translate relative to the track member. This allows the cutting block to be selectively positionable in more than one position while the track member remains in a single position.

A second embodiment includes a saw blade for resecting a portion of an anatomy. The saw blade comprises a first end having a tool engaging section extending along a first longitudinal axis. The saw blade further comprises a second end having a cutting head defining a plurality of cutting teeth, and extending along a second longitudinal axis. A neck portion interconnects the cutting head and the tool engaging section. The first and second longitudinal axes intersecting at the neck portion. The first axis and the second axis are disposed such that the cutting head is laterally offset from the tool engaging section.

A third embodiment includes a kit for resecting a portion of an anatomy. The kit comprises at least one saw blade including a cutting head and a neck portion and a guide block assembly including a track member and a cutting block. The track member includes a fixation section to fix the track member to a structure and a track translation section. The cutting block includes a guiding section adapted to guide a member and a guide translation section to operably engage the track translation section. The track translation section and the guide translation section operably engage to allow the cutting block to translate relative to the track member.

A fourth embodiment includes a method for resecting a boney portion of an anatomy that is surrounded by soft tissue. The method comprises creating an incision in the soft tissue surrounding the boney portion. A saw blade is selected to resect a first portion of the boney portion. A guide rail is mounted in a first rail position relative the boney portion. A cutting block is positioned in a first cutting block position relative to the guide rail to guide the saw blade. The cutting block is moved to a second cutting block position relative to the guide rail, such that the cutting block guides the saw blade in the second cutting guide position while the guide rail remains in the first rail position.

Further areas of applicability will become apparent from the detailed description provided hereinafter. It should be understood that the detailed description and specific examples, while indicating various embodiment of the invention, are intended for purposes of illustration only and are not intended to limit the scope of the following claims.

BRIEF DESCRIPTION OF THE DRAWINGS

The present description will become more fully understood from the detailed description and the accompanying drawings, wherein.

DETAILED DESCRIPTION OF VARIOUS EMBODIMENTS

The following description of various embodiments is merely exemplary in nature and is in no way intended to limit the appended claims, its application, or uses. Although the following various embodiments are illustrated in use with a knee joint and/or minimally invasive surgery, it will be understood that the tools and methods described herein can be used in conjunction with any other joint on any surgical procedure. For example, the saw blades and the cutting block may be used to resect the shoulder, elbow, or other similar joints in the anatomy. Therefore, the following description relating to a knee joint is merely exemplary and not intended to limit the scope of the following claims.

Figure 1:
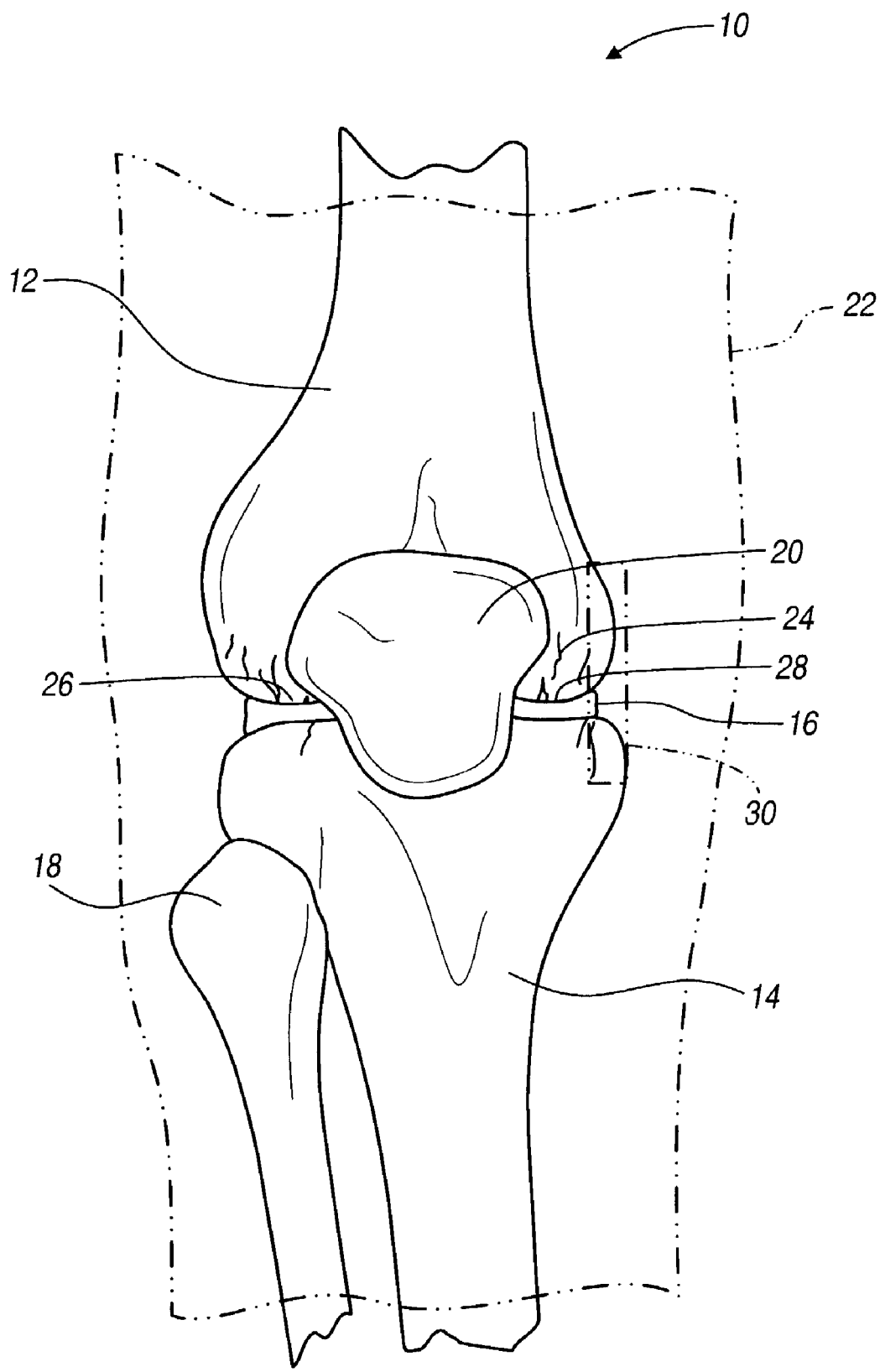
FIG. 1 is an anterior view of a right knee of a human anatomy.

With reference to FIG. 1, a knee joint 10 of a human anatomy includes a femur 12, which articulates with a tibia 14. Disposed between the femur 12 and the tibia 14 is a meniscus 16, which cushions the articulation and provides a bearing between the two boney portions or structures. The knee joint 10 further includes a fibula 18 and a patella 20. Surrounding the knee joint 10 is a soft tissue 22, which includes muscle, adipose tissue, and the epidermis. To perform any procedures on the internal components of the knee joint 10, the soft tissue 22 must be pierced. The femur 12 includes a first condyle 26 and a second condyle 28. It will be understood that the first condyle 26 may be a lateral condyle when the knee is a right knee, such as the knee illustrated in FIG. 1. It will be understood that the following discussion and instruments may also applicable to a left knee as well.

The knee joint 10 may become damaged or injured such that small fractures 24 or other injuries or deteriorations occur. When such injuries become great enough, the knee joint 10 may be resected and a prosthetic implanted to replace the articulating portions. The first and second condyles 26, 28 define an inferior surface of the femur 12. Moreover, the femur 12 is generally rounded and includes arcs and rounded surfaces of the first and second condyles 26, 28 on the inferior side of the femur 12. These convex surfaces provide for easy articulation of the femur 12 with the tibia 14. Similarly, convex surfaces are defined by the femur 12 on the anterior 12b and posterior 12c (shown in FIG. 6) sides as well. However, to implant a prosthetic, it is generally easier and more efficient to mount the prosthetic to substantially planar surfaces. Therefore, the convex surfaces of the femur 12 are resected before implanting a prosthetic. To provide such a resection, an incision 30 is made through the soft tissue 22 to gain access to the knee joint 10 (in FIG. 6). Though various styles and methods of making the incision 30 are known, it is desired to provide a less invasive incision 30. Therefore, the incision 30 is generally between about 1 cm and about 10 cm in length to provide access to the knee.

Because the incision 30 is made through the soft tissue 22, the incision 30 may be a small size and moved relative to the femur 12 and the tibia 14 to perform the procedure. Nevertheless, the smaller incision 30, the less trauma provided to the soft tissue 22. Because of the small incision 30, the instruments provided to resect the knee joint 10 are designed to efficiently perform their tasks without further traumatizing the soft tissue 22 and able to fit through the incision 30.

Figure 2:
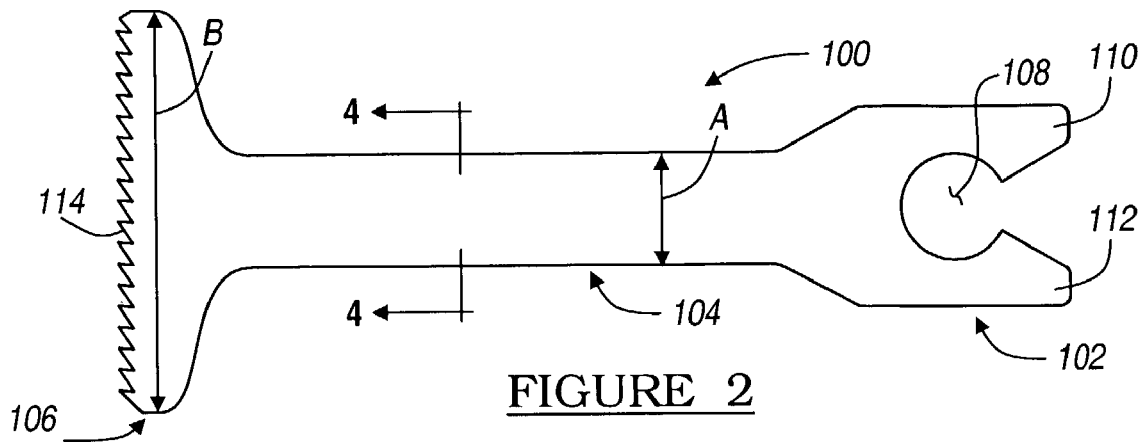
FIG. 2 is a plan view of a narrow saw blade according to one embodiment.

With reference to FIG. 2, a saw blade 100 for resecting a portion of the knee joint 10 is illustrated. The saw blade 100 may be used to resect the inferior portion of the femur 12, including the first and second condyles 26, 28 or the superior portion of the tibia 14. The saw blade 100 includes a tool engaging end or section 102, a body or neck 104, and a cutting head 106. The tool engaging end 102 includes a tool receiving notch 108, which is defined by a first leg 110 and a second leg 112. In this way, a portion of a power tool (not illustrated, but generally known) can be received within the tool receiving notch 108 to operate the saw 100 within the knee joint 10. It will be understood that any appropriate means or design may be used to affix the saw blade 100 to any appropriate tool. The tool engaging notch 108 is simply exemplary of any numerous method, which may be used to properly affix the saw blade 100 to a power tool. Other exemplary methods include a compression fit with a set screw or a bore formed in the saw blade 100, which would receive a set screw, but not include a notch. Therefore, the illustration of the exemplary tool engaging notch 108 is not intended to limit the present disclosure or the following claims. Furthermore, the tool engaging end 102 may be any appropriate size, including any appropriate width or depth to be properly received within a power tool. For example, the power tool may require that the tool engaging end 102 of the saw blade 100 be at least 1.5 cm in width. Therefore, the tool engaging end 102 may be at least 1.5 cm in width.

The neck 104 of the saw blade 100 has a width A which is selected to be narrower than a width B of the cutting head 106. Although width A of the saw blade 100 can be any appropriate width, it is generally selected to be relatively small to lessen abrasion and trauma to the soft tissue 22 defining the incision 30. This design also increases utility of a cutting guide as described more fully herein.

Figure 3:
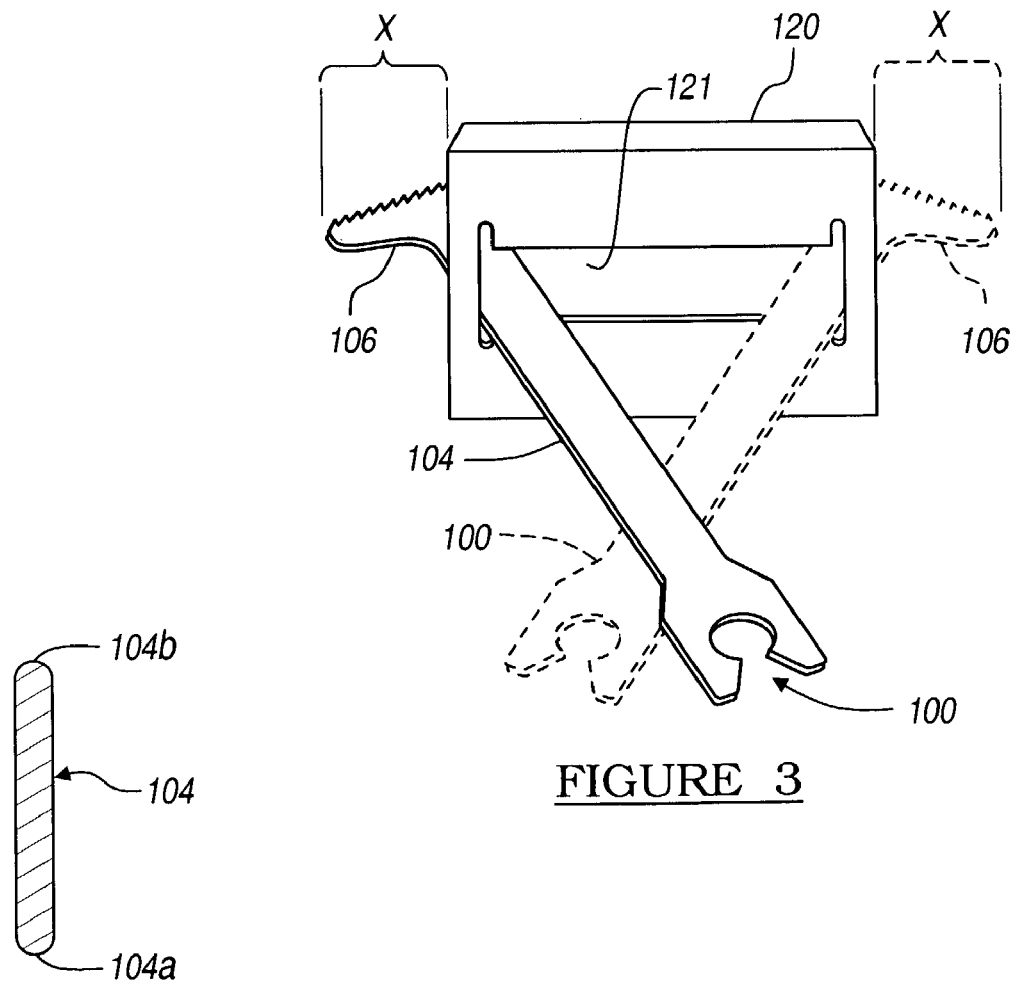
FIG. 3 is a perspective view of the saw blade in conjunction with a guide or cutting block.

With continuing reference to FIG. 2 and additional reference to FIG. 3, the width A of the neck 104 also allows a greater area to be resected by the saw blade 100. Specifically, as illustrated in FIG. 3, the narrow width A of the neck 104 allows the cutting head 106 to resect an area which is beyond the width of a cutting block 120. Because of the narrow width A of the neck 104, the cutting head 106 is able to easily resect an area at least a distant X beyond the edge of the slot 121 defined by the cutting block 120. The slot 121 defines a guide area of the cutting block 120. A saw blade including a neck and cutting head of equal widths limits the amount of area that a user is able to resect outside of the width of the slot 121. The narrow neck 104, however, allows the distance X to be resected outside of the width of the slot 121. The saw blade 100 is able to resect the distance X on both sides of the cutting block 120 during use.

Even though the neck 104 may have a selected width A, the cutting head 106 may have a different selected width B. Defined on the distal end of the saw blade 100 are cutting teeth 114. The cutting teeth 114 move in conjunction with the cutting head 106 and provide a sawing action to saw and remove material that is to be resected. The cutting teeth 114 may be any appropriate design or shape to provide the desired resection, speed or efficiency. Nevertheless, the width B of the cutting head 106 may be selected to allow for a greater cutting width than the width of the neck A. Although, the width A of the neck 104 may be selected to be smaller than the width of the retracted incision 30, the width B of the cutting head 106 may be selected to be greater than the width of the incision 30. For example, the width B of the cutting head 106 may be at least twice as big of the width A of the neck 104. This provides a cutting area, that is greater than the width of the neck 104, while minimizing trauma to the soft tissue 22.

Figure 4:
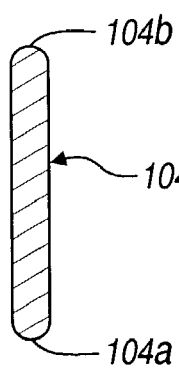
FIG. 4 is a cross-sectional view of the saw blade taken along line 4-4.

With continuing reference to FIG. 2, and additional reference to FIG. 4, the neck 104 of the saw blade 100 includes a first side 104a and a second side 104b. The edges or sides 104a and 104b of the neck 104 may include convex or other smooth non-angular shapes. The smooth and non-angular shapes further minimize trauma to the soft tissue 22 during operation. Simply, the saw 100 vibrates back and forth to move the cutting teeth 114. Even though the width A of the neck 104 is less than the width of the retracted incision 30, the edges 104a and 104b of the neck 104 may still contact the soft tissue 22. Therefore, removing the harsh or angular edges of the neck 104 help minimize trauma, to the soft tissue 22.

Figure 5:
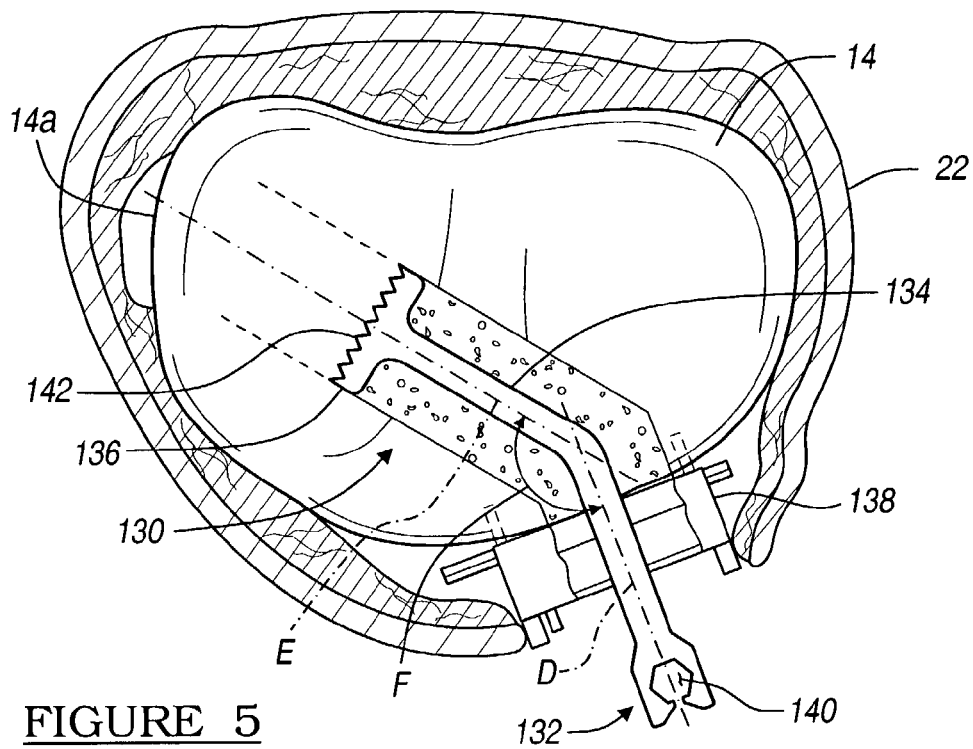
FIG. 5 is an elevational view of a portion of a tibia and an angled saw blade according to a second embodiment.

With reference to FIG. 5, an angled saw blade 130 including a tool engaging end 132, a neck 134, and cutting head 136 is illustrated. The saw blade 130 may be used in conjunction with a cutting block (illustrated herein), which is mounted relative the tibia 14 for the procedure. An incision is made in the soft tissue 22 to allow access of the saw 130 to the tibia 14. The tool engaging end 132 may include a power tool engaging notch 140, such that a power tool may operate the saw blade 130. In addition, the cutting head 136 defines a plurality of cutting teeth 142. Similar to the saw blade 100, the neck 134 of the saw blade 130 may have a width, which is less than the width of the cutting head 136. In addition, the width of the neck 134 may be less than the width of the incision 30 made in the soft tissue 22.

The tool engaging end 132 defines a first longitudinal axis D. In addition, the neck 134 defines a second longitudinal axis E. The first longitudinal axis D of the tool engaging body 132 is angled relative to the second longitudinal axis E of the neck 134. The angle F between the two axes may be any appropriate angle. For example, the angle F may be an obtuse angle to provide access to both sides of the tibia 14. The angle F allows an incision 30 to be placed on a selected side of the tibia 14 through the soft tissue 22. For example, if the tibia 14 is the right tibia, the incision may be formed medially relative to the tibia 14 (as in FIG. 1). If the saw blade 100 were only used, it would be difficult to resect the lateral side 14a of the tibia 14. The saw blade 100 would need to be moved relative to the tibia 14 to reach the lateral side 14a. This may cause trauma to the soft tissue 22 by moving the saw blade 100 or a cutting block. Especially if a cutting block were fixed relative the tibia 14, it would be very difficult and require additional time to move a cutting block relative the tibia 14. With the use of the angled saw blade 130, the lateral side 14a of the tibia 14 can be easily reached with the cutting teeth 142.

The angle F allows the cutting head 136 to be positioned in a space not aligned with the first longitudinal axis C of the tool engaging end 132. This allows the cutting teeth 142 to cut an area of the tibia 14, which is not aligned with the axis D. It will understood that the angled saw blade 130 may also be angled in the opposite direction. This will allow for the angled saw blade 130 to enter the knee area on the lateral side and reach to the medial side of the tibia 14. Regardless of the size of the angle F or the direction of the angle F, the angled saw blade 130 allows the cutting teeth 142 to cut an area that is not aligned with the longitudinal axis of the tool engaging body 132.

Figure 6:
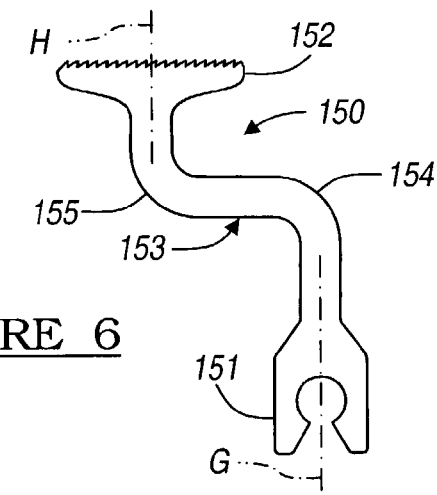
FIG. 6 is a plan view of an offset saw blade according to an embodiment.

With reference to FIG. 6, an alternative angled saw blade or offset saw blade 150 is illustrated. The offset saw blade 150 includes a tool engaging section 151, a cutting head 152, and a neck portion 153. The neck portion 153 includes a first angle or bend 154 and a second angle or bend 155. This allows the cutting head 152 to be laterally offset from the tool engaging section 151 without being angled thereto. More specifically, the tool engaging section 151 extends along a first or tool engaging section axis G while the cutting head 152 extends along a second or cutting head longitudinal axis H. The first axis G is laterally offset from the second axis H, but is parallel thereto. Therefore, the offset saw blade 150 can resect a portion of anatomy not in line with the cutting section 151 yet parallel therewith. The angled sections 154 and 155 may also be referred to or illustrated as "steps" of the neck portion 153.

Figure 7A:
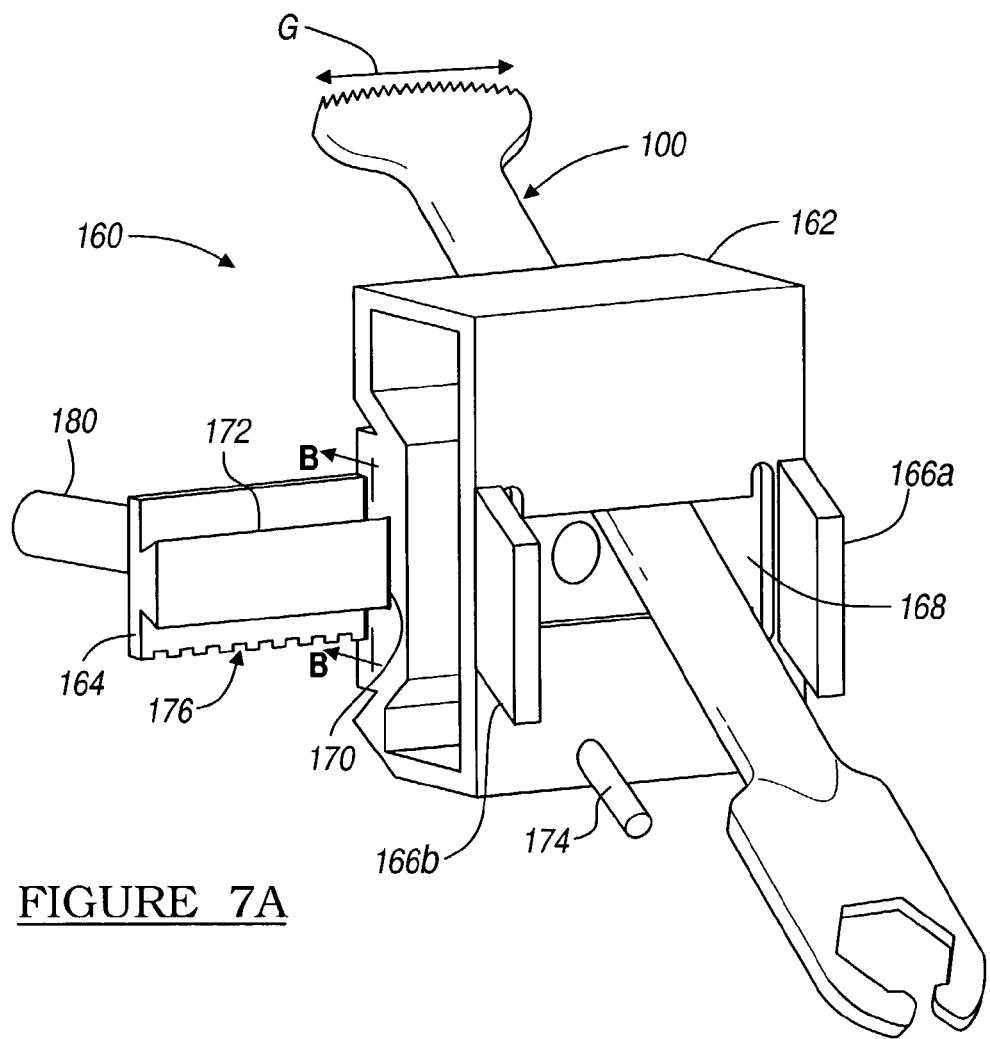
FIG. 7A is a perspective view of a cutting block assembly with a saw blade disposed therethrough.
Figure 7B:
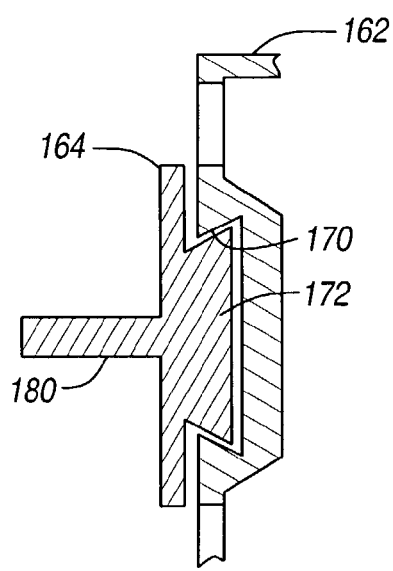
FIG. 7B is a cross-section taken along the line B-B of FIG. 7A.

With reference to FIGS. 7a and 7b, a sliding or translating cutting block assembly 160 is illustrated. The translating cutting block system 160 includes a cutting block 162, which is able to translate or slide on a rail or track member 164. The cutting block 162 includes a post or wall 166a and 166b, which is adapted to push the soft tissue 22 away from a saw blade bore 168 during use, as described further herein. Formed through the cutting block 162 is the saw blade bore 168. Although the cutting block 162 is illustrated to define a saw blade bore or slot 168, which acts as a saw blade guide, as described further herein, a saw blade bore 168 is not required for a cutting block 162. Specifically, the cutting block 162 may also only define surfaces which are used as cutting guides. Therefore, rather than placing the saw blade 100 through a slot formed in the cutting block 162, the saw blade 100 would only ride or translate along a surface of the cutting block 162 to direct the saw blade during use. Therefore, it will be understood that a saw blade bore 168 may define a guiding section or a surface of the cutting block 162 alone may define a guiding section.

Cutting blocks for resection, similar to the cutting block 162 are generally known, such as the 4-IN-1 CUTTING BLOCK, supplied by Biomet, Inc. of Warsaw, Ind. The cutting block 162 guides the saw blade 100 or 132 during a resection procedure to ensure that the proper areas of the boney portions are cut during the resection. However, the cutting block 162 is able to translate medially/laterally, by riding on the rail 164.

Specifically, the cutting block 162 includes a rail engaging section 170, which may define a female dove tail. Likewise, the rail 164 includes a rail translation section 172, such as a complimentary male dove tail. The rail engaging section 170 operably engages the rail translation section 172 so that the cutting block 162 is not able to substantially distract from the rail 164. Nevertheless, the cutting block 162 is able to move medial/laterally in the direction of arrow G by moving along the rail 164. It will be understood that the rail translation section 172 may define any portion complimentary to the guide or cutting block translation portion 170 to allow the cutting block 162 to translate relative the rail 164. For example, the rail translation section 172 may define a "T" shaped projection or a recess. Therefore, the guide translation portion 170 would be complimentarily shaped to engage the rail translation portion 172 for translation of the cutting block 162.

Although the cutting block 162 may be translated along the rail 164, the cutting block 162 may also be selectively locked relative the rail 164, if desired. The cutting block 162 may include a locking pin 174, which can be depressed to engage notches 176 formed in the rail 164. The locking pin 174 may be engaged or unengaged in any position, which can be selected by a user by depressing the locking pin 174. This allows the cutting block 162 to be moved to a selected position relative the rail 164 and locked in place while the saw blade 100 is used. It will be understood that alternative means of locking the cutting block 162 in a selected position can also be used. For example, a set screw can be set against any position on the rail 164 to lock the cutting block 162 in a selected position. This allows for a substantially infinite selection by a user. Alternatively, no locking portion may be provided, such that the cutting block 162 is always free to move, depending upon the selections of the user.

Figure 8:
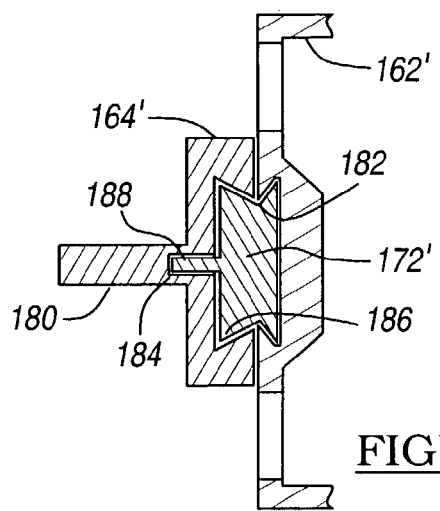
FIG. 8 is a cross-sectional view of a rail assembly according to an alternative embodiment.

With reference to FIG. 8, an alternative rail or track member 164' is illustrated. The rail member 164' similarly includes the bone anchor portion 180. The rail member 164', however, includes a track translation receiving area 182. The rail member 164' may also include an engaging section 184. The track translation section 172' defines a complimentary engaging section 186 to engage the rail member 164'. In addition, a pin 188 may extend from the track translation section 172' to engage the track translation receiving portion 184. In this embodiment, the rail member 164' engages a separate track translation section 172'. Therefore, a plurality of track translation sections 172' may be provided with the track member 164' and a selection may be made by a user.

Figure 9:
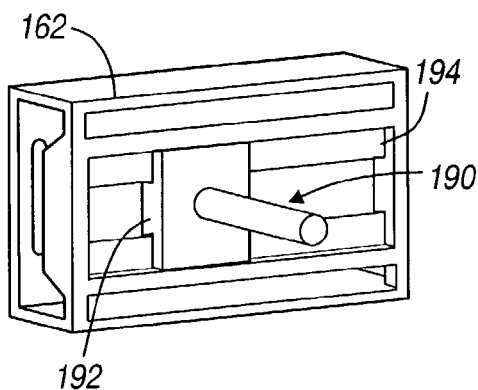
FIG. 9 is a perspective view of a cutting block and rail assembly according to an alternative embodiment.

With reference to FIG. 9, a second alternative rail 190 is illustrated. The rail 190 includes a rail translation section 192 which is shorter than the length of the cutting block 162. The cutting block 162 defines a cutting block translation section 194 which is longer than the rail translation section 192. In this embodiment, movement of the cutting block 192 is allowed because the block translation section 194 is longer than the rail translation section 192. In this manner, the rail 190 need not be longer than the cutting block 162 to allow the cutting block 162 to translate relative the rail 190.

Figure 10A:
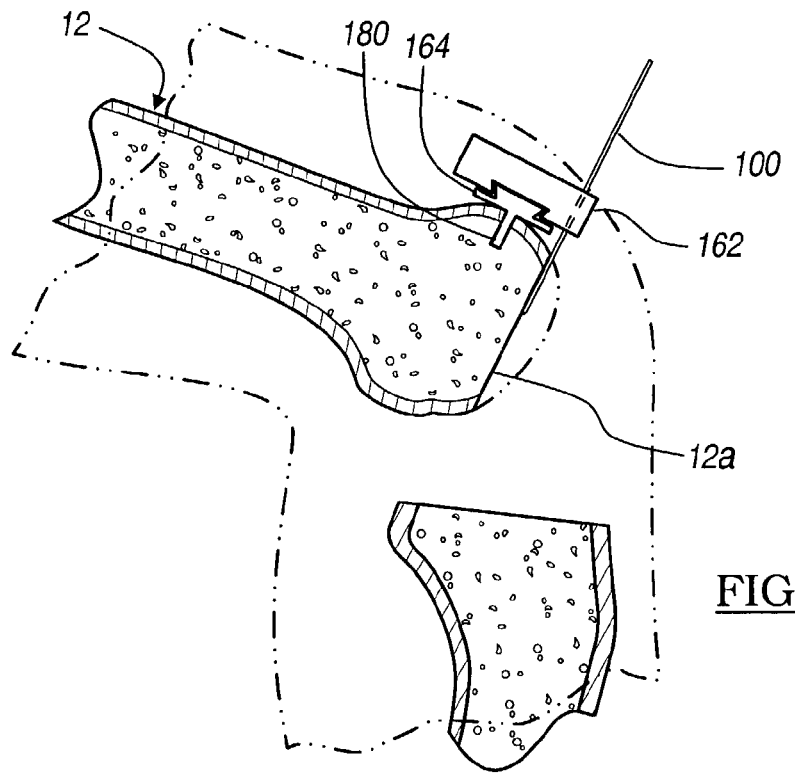
FIG. 10A is a side elevational view of a femur including the cutting block assembly, according to an embodiment, attached thereto.

As illustrated in FIG. 10, the rail 164 is mounted to a selected area of the boney portion, such as an inferior side 12a of the femur 12 or a portion of the tibia 14 using at least one of a plurality of mounting posts 180. The mounting posts 180 are fit into predrilled holes or bores formed into the femur 12. Specifically, the rail 164 is mounted directly to the femur 12. Therefore, the cutting block assembly 160 is mounted to a boney structure inside the soft tissue 22. Screws may also be used to tighten the posts 180 in place by providing a bore through the post 180. Alternatively, semi-permanent cements or adhesives may be used to fix the posts 180 in place. Other methods may also be used to fix the track 164 in place such as self-driving and tapping screws may-be passed through bores formed in the rail 164 to mount the rail 164 in a selected position. It will be understood that any appropriate method may be used to fix the rail 164 to a selected position. Regardless, the rail 164 allows the cutting block 162 to translate to a selected position.

The interaction of the track translation section 172 and the guide translation portion 170 may be substituted with any other proper engagement. For example, the rail 164 may define a male "T" cross-section, which is engaged by a female "T" cross-section formed on the cutting block 162. Any appropriate engagement between the rail 164 and the cutting block 162 may be provided, as long as the cutting block 162 is able to translate relative the rail 164, yet not substantially distract from the rail 164 during or after the translation. It will be understood, however, that the cutting block 162 may distract from the rail 164 if selected. For example, the cutting block 162 may translate relative the rail 164 by distracting the cutting block 162 from the rail 164 and moving the cutting block 162 relative thereto. Moreover, if the cutting block 162 is not locked relative the rail 164, it may be selected that the cutting block 162 distracts from the rail 164 to allow for greater freedom of movement of a user of the cutting block 162.

With continuing reference to FIGS. 7A-10C, a method of using the translating cutting block 160 and the saw blade 100 is illustrated. If it is selected that the knee 10 requires a resection, the incision 30 is made near the knee 10 to allow access to the knee 10 by the various instruments. Once the incision 30 is made, the distal or inferior end 12a of the femur 12 is first resected to form a substantially flat and planar region. To form the substantially planar resection of the inferior end 12a of the femur 12, the cutting block assembly 160 is fixed to an anterior side 12b of the femur 12. The saw blade 100 is then guided with the cutting block 162 through the incision 30 to form the distal cut on the distal end 12a of the femur 12. The interaction of the cutting block 162 and the rail 164 allows the cutting block 162 to be translated medial laterally relative to the femur 12. Moreover, as described above and further herein, because the cutting block 162 is able to translate relative the rail 164, the cutting block 162 can be minimized in size. That is, the cutting block 162 need not be the width of the femur 12 required to be resected because the cutting block 162 is able to move medial laterally relative the femur 12. This resection substantially removes the condyles 26 and 28 and forms a substantially flat area to form the first resection portion of the knee 10 resection.

Figure 10C:
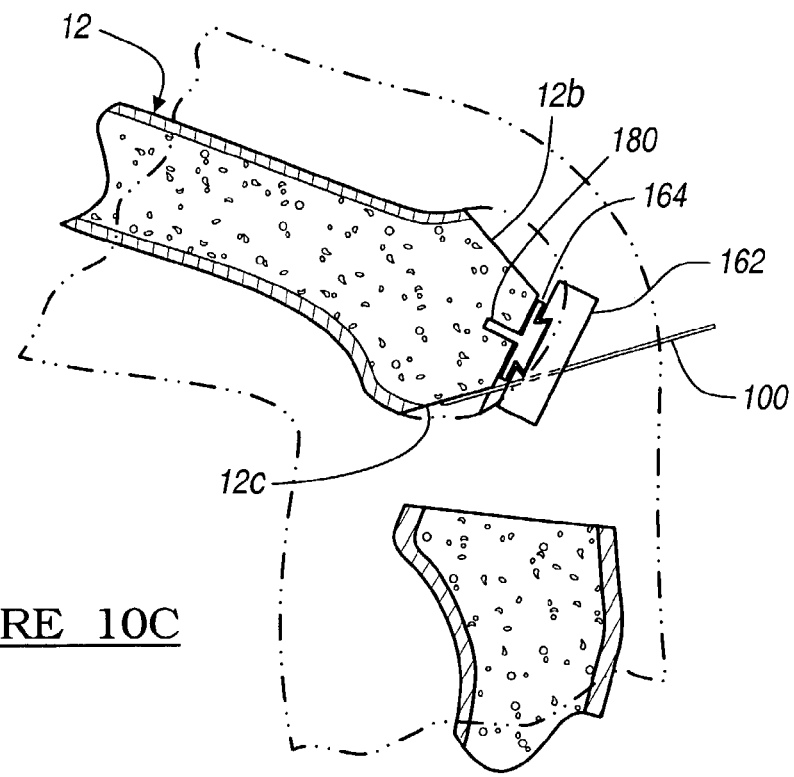
FIG. 10C is a cross-sectional view of the cutting block assembly affixed to a distal end of a femur.
Figure 10B:
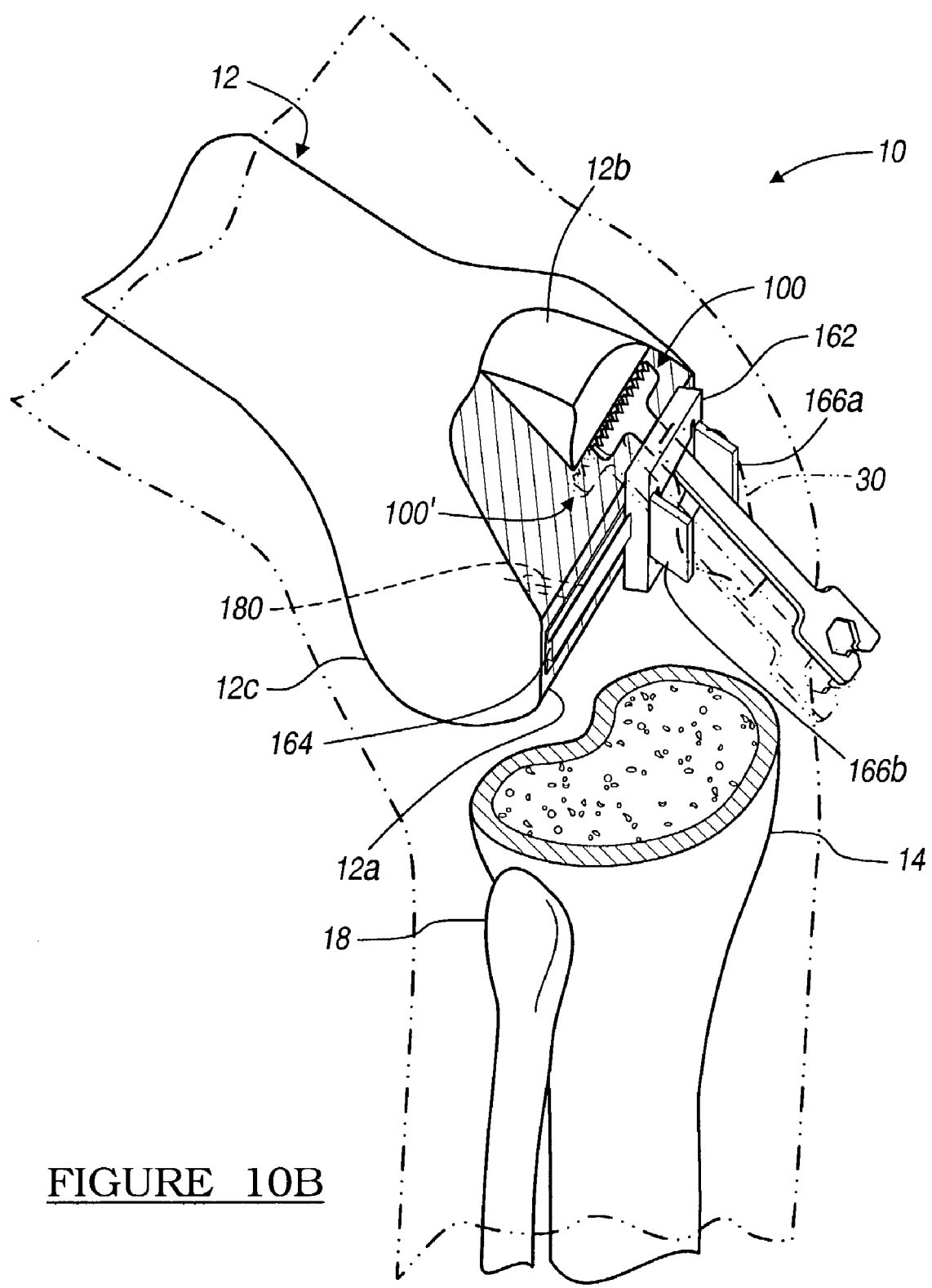
FIG. 10B is a perspective view of a knee joint illustrating an exemplary use of the cutting block and saw blade.

As specifically illustrated in FIGS. 10B and 10C, after the inferior end of the femur 12a is resected, the cutting block assembly 160 can be mounted thereto. Specifically, the rail 164 is mounted to the femur 12 using the mounting posts 180. This allows the rail 164 to be substantially fixed relative the femur 12 for use of the cutting block 162. The cutting assembly 160 is inserted through the incision 30 and mounted to the inferior end 12a of the femur 12. This allows the cutting block 162 to translate medially/laterally while mounted on the rail 164, which is mounted or fixed to the femur 12. The cutting block 162, as is generally known, allows for resection of the anterior side 12b and posterior side 12c of the femur 12. Similarly, the saw blade 100 can be inserted through the cutting block 162 to resect the posterior side 12c of the femur 12. Therefore, the exemplary illustration resecting the anterior side 12b of the femur 12 is not meant to limit the following claims.

After the cutting assembly 160 is mounted to the femur 12, using proper methods, such as adhesives or screws, the saw 100 can be inserted through the incision 30 and through the cutting block 162. This allows the saw 100 to be properly aligned relative to the femur 12 using the cutting block 162. Therefore, the saw blade 100 can resect portions of the anterior side 12b of the femur 12. Due to the narrowness of the neck 104 of the saw blade 100, the incision 30 may be small, even though the saw blade 100 must move from side to side to resect portions of the femur 12. For example, the saw blade 100 illustrated in solid lines, shows the position of the saw blade before it moves to resect a portion of the femur 12. The saw blade 100', shown in phantom lines, illustrates a portion of the vibrational motion of the saw blade 100 while in operation. The narrow neck 104, however, does not substantially engage the edges of the incision 30 during this process. Therefore, the trauma to the soft tissue 22 is minimized due to the narrow neck 104. Similarly, the cutting block 162 and cutting assembly 160 as a whole is minimized in size to reduce trauma to the soft tissue 22 during the positioning and removal of the cutting assembly 160.

After the saw blade 100 has been used to resect a portion, for example the lateral side, of the femur 12, which it is able to reach in a first position, the cutting block 162 can be translated along the rail 164 to a second position. In this second position, the cutting block 162 may be held or locked in place with the locking pin 174. Alternatively, no locking mechanism may be used to allow the cutting block 162 to move freely depending upon the desires of the user. Nevertheless, the cutting block 162 may translate to the medial side of the knee 10, as the knee 10 illustrated in FIG. 6 is a right knee, such that the saw blade 100 is able to easily resect the medial side of the femur 12.

The saw blade 100 may be positioned to cut the anterior side 12b of the femur on the medial side of the femur 12. In this way, the rail 164 needs only be mounted once while the cutting block 162 can be translated along the rail 164 to cut all the necessary portions of the anterior side 12b of the femur 12. Similarly, the cutting block 162 may be removed and rotated to cut the posterior side 12c of the femur 12 with the saw blade 100. An appropriately configured cutting block 162 allows the saw blade 100 to resect both the anterior 12b and the posterior 12c of the femur 12 without rotating the cutting block 162.

Extending from the cutting block 162 are the soft tissue holders or pushers 166a and 166b. The soft tissue pushers 166a and 166b are positioned to ensure that the soft tissue 22 does not intersect the guide bore 168 of the cutting block 162. Moreover, the soft tissue pushers 166a and 166b help move the incision 30 relative the femur 12 during the procedure. Specifically, the incision 30 is a substantially small incision, such that the instruments may be inserted into the knee 10, but not so large as to produce large amounts of trauma to the soft tissue 22. Nevertheless, the movement of the cutting block 162 can move the incision 30 and the surrounding soft tissue 22 relative the femur 12 to allow for the cutting block 162 to easily move along the rail 164. In this way, the cutting block 162 helps reduce trauma to the soft tissue 22 surrounding the knee 10. It will be understood that any appropriate saw blade may be used in conjunction with the cutting block 162, therefore the cutting assembly 160, it is not necessarily exclusive to use with the narrow saw blade 100.

With reference to FIG. 10C, the femur 12 is illustrated resected such that the anterior side 12b has been resected to form a substantially flat and planar portion. In addition the posterior side 12c of the femur 12 has also been resected. The saw blade 100 has been inserted through the cutting block 162 to resect the posterior side 12c of the femur 12. In this way, the rail 164 need only be mounted once to resect both the anterior side 12b and the posterior side 12c of the femur 12. Moreover, the use of the translating cutting block 162 allows the rail 164 to be positioned only once to resect both the medial and lateral portions of the femur 12 as well. This allows the rail 164 to be mounted only once to the femur 12 to resect all portions of the anterior side 12b and the posterior side 12c. This assists in reducing trauma to the femur 12 during the resection procedure and can decrease healing time after the procedure is completed.

Figure 11:
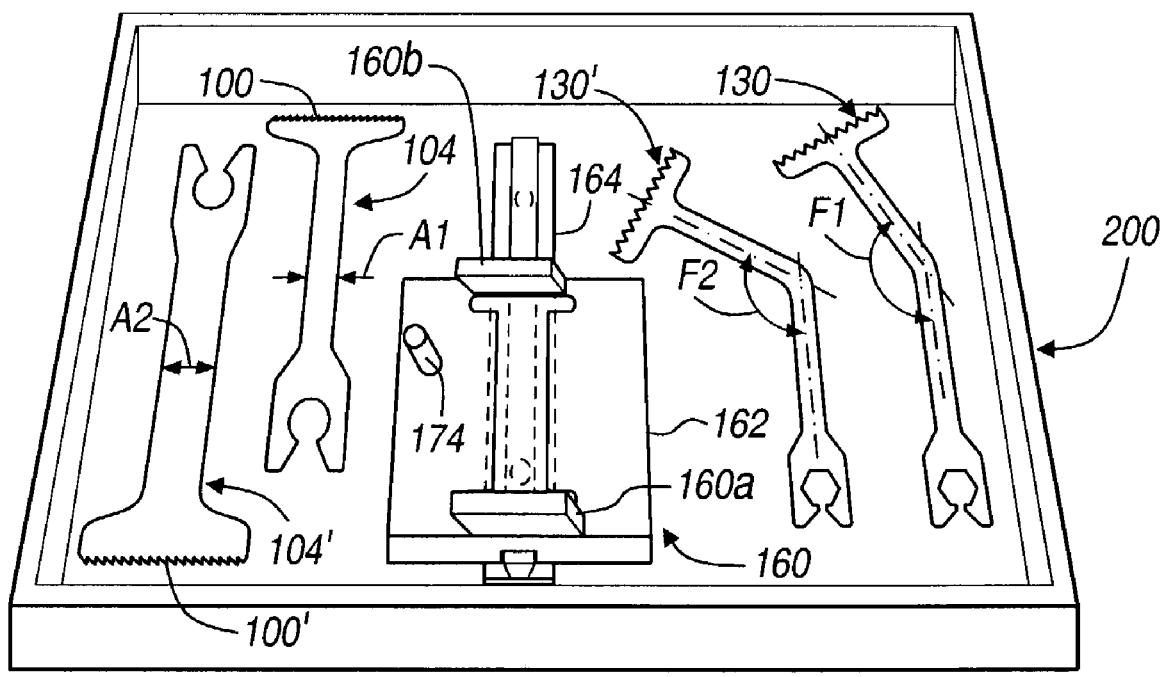
FIG. 11 is a perspective view of a kit including various saw blades and a cutting block assembly.

With reference to FIG. 11, a kit 200 includes a plurality of the saw blades 100 and 130 and the translating cutting block assembly 160. The kit 200, for example, may include a first narrow cutting saw 100 and a second narrow cutting saw 100'. The first narrow cutting saw 100 may include a neck 104, which includes a width $A_1$. The width $A_1$ can be any selected width to be used in a resection procedure. The kit 200 may also include a second narrow saw 100', which has a neck 104', and includes a second width $A_2$. The second width $A_2$ may be greater than the width $A_1$ of the first narrow saw blade 100. Therefore, the physician may select the desired narrow saw blade, 100 or 100', depending upon the specific procedure to be performed. For example, a larger incision may be used or necessary that may accept the larger width $A_2$ of the second narrow saw blade 100'. Nevertheless, a selection is left to the user depending upon the desires or necessity.

Similarly, the kit 200 may include a first angled saw blade 130, that includes an angle $F_1$ of a longitudinal axis of the neck relative to the longitudinal axis of the tool engaging section. The kit 200 may also include a second angled saw blade 130', which includes a second angle $F_2$. The second angle $F_2$ may be greater or less than the first angle $F_1$. Therefore, the plurality of the angled saw blades 130 and 130', allows one to be selected depending upon the particular anatomy of the patient or desires of a physician. Moreover, the various angles can more easily reach various portions of the knee 10 without great effort or trauma to the soft tissue 22. For example, the first angle saw blade 130 may be used to resect a first portion of the knee 10 while the second angle saw blade 130' is used to resect a second portion of the knee 10. Therefore, both of the angled saw blades 130 and 130' can be used to resect the various portions of the knee 10. It will be understood that although only two exemplary saw blades for the narrow saw blade 100 and 100' and the angled saw blade 130 and 130' a larger plurality of the various saw blades may be provided in the kit 200.

Also provided in the kit 200 is the cutting block assembly 160. The cutting block assembly 160 includes the rail 164 and the cutting block 162. As described above, the cutting block 162 is able to translate on the rail 164 to resect the various portions of the anatomy. The cutting block assembly 160 can be used in conjunction with the narrow saw blades 100 and 100' or other generally known saw blades. The cutting block assembly 160 may also be used in conjunction with the angled saw blades 130 and 130' if desired. Nevertheless, the resection kit 200 can be provided for use in a surgery. Therefore, during the operative procedure, the various saw blades can be selected and used by a physician in conjunction with the cutting block assembly 160.

The description is merely exemplary in nature and, thus, variations that do not depart from the gist of the description are intended to be within the scope of the following claims. Such variations are not to be regarded as a departure from the spirit and scope of the following claims.

What is claimed is:

1. A guide block assembly for use in assisting resecting a boney structure, the assembly comprising:
a track member to be fixed relative to the boney structure including:
a fixation section to fix said track member relative to the boney structure; and
a track translation section having a first end and a second end and a first dimension therebetween; and
a cutting block including:
at least two guiding sections each including a surface adapted to guide a cutting member; and
a guide translation section operable to engage said track translation section;
wherein said track translation section and said guide translation section operably interact to allow said cutting block to translate relative to said track member so that at least a portion of said cutting block is operable to translate a translation dimension greater than the first dimension and past at least one of the first end or the second end;
wherein said cutting member includes an elongated saw having a neck portion and a cutting head;
wherein said neck portion is operably engaged in one of said at least two guiding sections to guide said cutting head during use; and
wherein said neck portion is narrower than said cutting head such that the cutting member generally defines a "T-Shape".

2. The guide block assembly of claim 1, wherein the track translation section includes a longitudinal length that defines an entire path of the cutting block;
wherein the cutting block is operable to be selectively positioned in a first position to make a first cut and operable to be selectively positioned in a second position to make a second cut while the track member remains in a single position, wherein the first position and the second position allow at least a portion of the at least two guiding sections to extend beyond the track translation section.

3. The guide block assembly of claim 2, wherein at least one of the first position, the second position, or combinations thereof positions at least one of the two guiding sections beyond a boundary of the track member.

4. The guide block assembly of claim 1, wherein said fixation section includes a member extending from said track member adapted to be inserted into the boney structure.

5. The guide block assembly of claim 1, wherein said track translation section includes at least one of a male dovetail, a male "T", or combinations thereof extending from said track member.

6. The guide block assembly of claim 1 wherein the at least two guiding sections of the cutting block have a second longitudinal dimension;
wherein the translation dimension is greater than a sum of the first dimension and the second dimension.

7. The guide block assembly of claim 1, wherein said guiding section defines a bore extending through said cutting block and displaced a distance away from said track member, wherein the guiding section and the track member are not coplanar, such that said cutting member is guided away from said track member to resect the boney structure.

8. The guide block assembly of claim 1, wherein:
said track translation section is selected from one of a slot or a rail;
said guide translation section is selected from the other of said slot or said rail.

9. The guide block assembly of claim 1, further comprising:
a locking member;
wherein said track member further includes locking portions operable to be selectively engaged by said locking member;
wherein said cutting block is fixed relative to said track member when said locking member is engaged in at least one of said locking portions.

10. The guide block assembly of claim 1, wherein said track translation section is selected to be either formed integrally with said track member, formed integrally with said cutting block, operably affixed to said track member, or operably affixed to said cutting block and
wherein said guide translation section is selected to be either formed integrally with said track member, formed integrally with said cutting block, operably affixed to said track member, or operably affixed to said cutting block.

11. The guide block assembly of claim 1, wherein said guiding section defines a second dimension, wherein the interaction of the track translation section and said guide translation section allows the guiding section to traverse a dimension greater than with the first dimension or the second dimension.

12. The guide block assembly of claim 1, wherein the first dimension is a complete longitudinal length of the track translation section.

13. The guide block assembly of claim 1, wherein the two guiding sections are positioned at an angle relative to one another that is greater or less than 90 degrees.

14. The guide block assembly of claim 1,
wherein the track translation section defines only a single elongated member having a first longitudinal edge and a second longitudinal edge;
wherein the cutting block includes a first block edge extending beyond the first longitudinal edge and a second block edge extending beyond the second longitudinal edge;
wherein a first guiding section of the at least two guiding sections is displaced a distance from both of the first longitudinal edge and the second longitudinal edge and a second guiding section of the at least two guiding sections is displaced a distance from both of the first longitudinal edge and the second longitudinal edge.

15. A guide block assembly for use in assisting a resection of a boney structure, the assembly comprising:
a track member to be held relative to the boney structure having a track translation section having a total length;
a cutting block defining a guide section to guide a cutting member; and
a guide translation section to engage said track translation section;
wherein the guide section defines a slot that includes a first surface and a second surface operable to bound the cutting member;
wherein said track translation section and said guide translation section interact to allow said cutting block to translate relative to said track member so that the guide section is operable to traverse a length greater than the total length.

16. The assembly of claim 15, wherein the cutting block is selectively moveable between a first position to make a first cut and a second position to make a second cut while the track member remains in a single position.

17. The assembly of claim 15, further comprising:
a fixation member to selectively fix said track member to the boney structure.

18. The assembly of claim 15, wherein said cutting block defines an outer edge and said guide section has a fixed surface that defines an angle relative to said outer edge.

19. The assembly of claim 15, wherein said guide section is operable to form an anterior chamfer cut and a posterior chamfer cut on the boney structure.

20. The assembly of claim 15, wherein said cutting block is moveable relative to the track member with the cutting member.

21. The assembly of claim 15, wherein the track member includes a terminal end; wherein at least a portion of the guide section is operable to pass the terminal end of the track translation section extending the total length.

22. The assembly of claim 15, wherein the guide section includes a guide surface that defines a guide area that defines a dimension greater than the total length.

23. The guide block assembly of claim 15, wherein the track translation section includes a translation axis that defines a path that extends a total length of the track member; wherein the cutting block defines a guide surface; wherein the cutting block is operable to move along the path so that the guide surface extends further than the total length.

24. The assembly of claim 15, wherein the first surface and the second surface define an area through which the cutting member is operable to pass before the cutting member engages the boney surface.

25. The assembly of claim 15, wherein the cutting member includes a cutting head portion defining a total cutting surface of the cutting member having a first width greater than a second width of a portion extending from the cutting head;
wherein the cutting member generally defines a "T-shaped" cutting member.

26. A guide block assembly for use in assisting a resection of a boney structure, the assembly comprising:
a track member to be held relative to the boney structure having a track translation section;
a cutting block moveable relative to the track member defining a first guide section extending along a first axis and a second guide section extending along a second axis at a non-zero angle relative to the first axis to guide a cutting member wherein the first guide section, the second guide section, or combinations thereof is defined by a slot; and
a guide translation section to engage said track translation section;
wherein at least one of the first guide section, the second guide section, or combinations thereof is operable to extend a distance beyond the track translation section.

27. The assembly of claim 26, further comprising:
a guide surface that is defined by no more than a single edge of said cutting block.

28. The assembly of claim 26, wherein said cutting block is dimensioned smaller than said track member.

29. The assembly of claim 26, wherein said guide section includes a slot defined through said cutting block.

30. The guide block assembly of claim 26, wherein the track member has a total distance defined by two ends of the track member and at least a portion of the cutting block is operable to translate a distance greater than the total distance.

31. The guide block assembly of claim 30, wherein the two ends are terminal ends of the track member.

32. The guide block assembly of claim 26, wherein the first guide section and the second guide section are angled so that the first axis and the second axis intersect on only one side of the track member.

33. The assembly of claim 26, wherein the non-zero angle is an angle less than 90 degrees or greater than 90 degrees.

34. A cutting member guide assembly for use in assisting in a resection of a boney structure with a cutting member, the assembly comprising:
a track member defined by a first end and a second end to be held relative to the boney structure having a track translation section having a first dimension along a longitudinal axis of the track member and extending from the first end to the second end;
a cutting block defining an internal guide section to guide a cutting member at a fixed non-zero angle relative to an outer edge of the cutting block; and
a guide translation section to engage said track translation section;
wherein said track translation section and said guide translation section interact to allow said cutting block to translate relative to said track member so that the guide section is operable to traverse a dimension greater than the first dimension.

35. The assembly of claim 34, wherein the first dimension is a linear dimension.

36. The assembly of claim 34, wherein the guide section is defined by at least a first surface and a second surface substantially defining a slot through which the cutting member is operable to pass.

37. The assembly of claim 34, wherein the cutting member includes a cutting head portion defining a total cutting surface of the cutting member having a first width greater than a second width of a portion extending from the cutting head;
wherein the cutting member generally defines a "T-shaped" cutting member.

38. The assembly of claim 34, wherein the track translation section defines only a single substantially straight path of translation;
wherein the guide translation section substantially restricts a movement of the cutting block along the path;
wherein the guide section defines a slot operable to allow the cutting member to pass through the slot to engage the boney structure substantially only along the path.

39. A guide block assembly for use in assisting resecting a boney structure, the assembly comprising:
a track member to be fixed relative to the boney structure including:
a fixation section to fix said track member relative to the boney structure; and
a track translation section having a first end and a second end and a first dimension therebetween; and
a cutting block including:
at least two guiding sections each including a surface adapted to guide a cutting member wherein the two guiding sections are positioned at an angle relative to one another that is greater or less than 90 degrees; and
a guide translation section operable to engage said track translation section;
wherein said track translation section and said guide translation section operably interact to allow said cutting block to translate relative to said track member so that at least a portion of said cutting block is operable to translate a translation dimension greater than the first dimension and past at least one of the first end or the second end.

40. A guide block assembly for use in assisting a resection of a boney structure, the assembly comprising:
- a track member to be held relative to the boney structure having a track translation section;
- a cutting block moveable relative to the track member defining a first guide section extending along a first axis and a second guide section extending along a second axis at a non-zero angle relative to the first axis to guide a cutting member, wherein the non-zero angle is an angle less than 90 degrees or greater than 90 degrees; and
- a guide translation section to engage said track translation section;
- wherein at least one of the first guide section, the second guide section, or combinations thereof is operable to extend a distance beyond the track translation section.

* * * * *